United States Patent [19]

Miller et al.

[11] 4,143,137

[45] Mar. 6, 1979

[54] SUBSTITUTED ARYLCYANOALKYL AND DIARYLCYANOALKYLIMIDAZOLE METAL SALT COMPLEXES AND FUNGICIDAL COMPOSITIONS AND METHODS UTILIZING THEM

[75] Inventors: George A. Miller, Maple Glen; Hak-Foon Chan, Doylestown; Harold E. Carley, Chalfont, all of Pa.

[73] Assignee: Rohm and Haas Company, Philadelphia, Pa.

[21] Appl. No.: 839,877

[22] Filed: Oct. 6, 1977

Related U.S. Application Data

[60] Division of Ser. No. 647,039, Jan. 7, 1976, Pat. No. 4,073,921, which is a continuation-in-part of Ser. No. 557,546, Mar. 12, 1975, abandoned.

[51] Int. Cl.² .......................... A01N 9/22; C07F 1/00; C07F 3/00; C07F 15/00
[52] U.S. Cl. ................................. 424/245; 424/273 R; 260/299; 548/336; 548/337; 548/341
[58] Field of Search ................ 260/299; 548/336, 337, 548/341; 424/245, 273

[56] References Cited

U.S. PATENT DOCUMENTS

| | | | |
|---|---|---|---|
| 3,285,921 | 11/1966 | Ortner et al. | 260/299 X |
| 3,677,978 | 7/1972 | Dowbenko et al. | 260/299 X |
| 3,732,242 | 5/1973 | Büchel et al. | 548/341 |
| 4,005,083 | 1/1977 | Büchel et al. | 424/245 |
| 4,073,901 | 2/1978 | Büchel et al. | 424/245 |
| 4,085,209 | 4/1978 | Miller et al. | 424/245 |
| 4,105,762 | 8/1978 | Miller et al. | 424/245 |

*Primary Examiner*—Donald G. Daus
*Assistant Examiner*—Diana G. Rivers
*Attorney, Agent, or Firm*—Bernard J. Burns; William E. Lambert, III; George W. F. Simmons

[57] ABSTRACT

This invention relates to substituted arylcyanoalkyl and diarylcyanoalkylimidazoles, their acid addition salts and their metal salt complexes and their use as broad spectrum protectant-eradicant fungicides.

14 Claims, No Drawings

SUBSTITUTED ARYLCYANOALKYL AND DIARYLCYANOALKYLIMIDAZOLE METAL SALT COMPLEXES AND FUNGICIDAL COMPOSITIONS AND METHODS UTILIZING THEM

This application is a division of U.S. application Ser. No. 647,039, filed Jan. 7, 1976, now U.S. Pat. No. 4,073,921 granted Feb. 14, 1978, which in turn is a continuation-in-part of U.S. application Ser. No. 557,546, filed Mar. 12, 1975, now abandoned.

The arylcyanoalkyl and diarylcyanoalkylimidazoles of this invention are highly active fungicidal agents against a broad spectrum of phytopathogenic fungi. Metal salt complexes of these compounds possess an additional utility in that they provide a safening effect (reduced phytotoxicity without a reduction in efficacy) in these highly active fungicidal agents.

This invention concerns the arylcyanoalkyl and diarylcyanoalkylimidazoles of the general formula

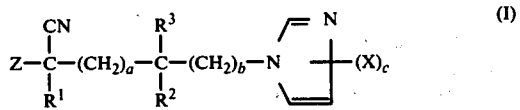

wherein Z is an aryl or substituted aryl group; $R^1$ is a hydrogen atom, an alkyl group, a cycloalkyl group, an alkenyl group, an alkynyl group, a cycloalkenyl group, phenyl or substituted phenyl group, an aralkyl or substituted aralkyl group; $R^2$ and $R^3$ are independently a hydrogen atom, an alkyl group, a phenyl or substituted phenyl group or an aralkyl or substituted aralkyl group or taken together form a ($C_4$-$C_8$) cycloalkyl group; $R^1$ and Z when taken together form the group

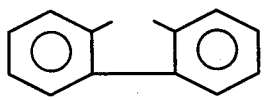

a and b are integers from zero to five; X is a halogen atom; c is an integer from zero to two and the agronomically acceptable acid addition salts thereof.

A further embodiment of this invention is the metal salt complexes of the general formula

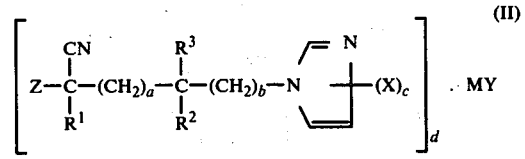

wherein Z, $R^1$, $R^2$, $R^3$, a, b, X and c are as above; M is a metal cation selected from Group IIA, IVA, IB, IIB, VIB, VIIB or VIII of the Periodic Table; Y is an anion counterion; and d is an integer from one to four.

In the above definition of the compounds of this invention the term "alkyl" denotes a ($C_1$-$C_{20}$) alkyl group preferably a ($C_1$-$C_8$) alkyl group which can be branched or straight chained. The term "aryl" denotes a phenyl, naphthyl, methylene-dioxyphenyl, thienyl, pyrryl, furyl, pyridyl or pyrimidyl group, preferably a phenyl, naphthyl, methylenedioxyphenyl, thienyl or pyridyl group, most preferably a phenyl group optionally substituted with up to three substituents preferably two substituents independently selected from the group consisting of fluoro, chloro, bromo, iodo, nitro, cyano, methoxy, ethoxy, methyl ethyl, propyl, butyl, trihalomethyl, phenyl and benzoyl. The term "aralkyl" as used in the above definition denotes a benzyl, phenethyl or naphthylmethyl group or a benzyl, phenethyl or naphthylmethyl group substituted with up to two substituents independently selected from the group consisting of fluoro, chloro bromo, iodo, nitro, cyano, methoxy, ethoxy, methyl, ethyl and trihalomethyl. The term "cycloalkyl" is meant to denote a ($C_3$-$C_8$) cycloalkyl group, and the term "cycloalkenyl" is meant to denote a ($C_5$-$C_8$) cycloalkenyl group.

A preferred embodiment of this invention is the compounds of Formula I wherein Z is phenyl optionally substituted with up to two substituents selected from the group consisting of fluoro, chloro, bromo, iodo, nitro, methoxy, and methyl; $R^1$ is hydrogen, ($C_1$-$C_{10}$) alkyl, ($C_3$-$C_8$) cycloalkyl, ($C_5$-$C_8$) cycloalkenyl, ($C_3$-$C_6$) alkenyl, ($C_3$-$C_6$) alkynyl, phenyl, benzyl or phenethyl or phenyl, benzyl or phenethyl substituted with up to two substituents selected from the group consisting of fluoro, chloro, nitro, methoxy or methyl; $R^2$ and $R^3$ are independently hydrogen, ($C_1$-$C_{10}$) alkyl, phenyl, benzyl or phenethyl or phenyl, benzyl or phenethyl substituted with up to two substituents selected from the group consisting of chloro, nitro, methoxy or methyl, or when taken together form ($C_4$-$C_8$) cycloalkyl; a is 0 to 5; b is zero; X is chloro; and c is zero to two and the agronomically acceptable acid addition salts and metal salt complexes thereof.

A more preferred embodiment of this invention is the compounds of Formula I wherein Z is phenyl or phenyl substituted with up to two substituents selected from the group consisting of fluoro, chloro, methyl, methoxy or nitro; $R^1$ is hydrogen, ($C_1$-$C_8$) alkyl, cyclohexyl, cyclohexenyl, ($C_3$-$C_6$) alkenyl, ($C_3$-$C_6$) alkynyl, phenyl or chlorophenyl, benzyl, chlorobenzyl or phenethyl; $R^2$ and $R^3$ are independently hydrogen, ($C_1$-$C_3$) alkyl or phenyl; a is 0 to 4; b is zero; c is zero and the agronomically acceptable acid addition salts and metal salt complexes thereof.

A most preferred embodiment of this invention is the compounds of Formula I wherein Z, b and c are as defined above and $R^1$ is ($C_1$-$C_4$) alkyl, phenyl, benzyl or phenethyl, $R^2$ and $R^3$ are hydrogen; and a is zero and the agronomically acceptable acid addition salts and metal salt complexes thereof.

Typical compounds which are encompassed by this invention are illustrated below:

1-[2-cyano-2-(2-chlorophenyl)propyl]imidazole
1-[2-cyano-2-(3-fluorophenyl)butyl]-2-methylimidazole
1-[2-cyano-2-(4-bromophenyl)pentyl]imidazole
1-[2-cyano-2-(2,3-difluorophenyl)3,3-dimethylbutyl]imidazole
1-[2-cyano-2-(5-bromo-2-chlorophenyl)dodecyl]imidazole
1-[3-cyano-3-(2,6-dichlorophenyl)tetradecyl]-2-methylimidazole
1-[5-cyano-5-(2,4,6-trichlorophenyl)pentadecyl]imidazole
1-[8-cyano-8-(2-nitrophenyl)heptadecyl]-2-chloroimidazole
1-[10-cyano-10-(2-chloro-4-nitrophenyl)octadecyl]imidazole
1-[2-cyano-2-(2-cyanophenyl)docosyl]-2-nitroimidazole
1-[2-cyano-2-(2-methoxyphenyl)hexyl]imidazole 1-[2-cyano-2-(4-chloro-2-nitrophenyl)butyl]-2-methylimidazole
1-[2-cyano-2-phenyl-2-(2-chlorophenyl)ethyl]imidazole
1-[2-cyano-2-(2-bromophenyl)-2-(2-nitrophenyl)ethyl]imidazole
1-[2-cyano-2-(2-chloro-4-methylphenyl)-2-(4-methoxyphenyl)ethyl]imidazole
1-[3-cyano-3-(2,6-diethylphenyl)propyl]-2-nitroimidazole
1-[2-cyano-2-(4-trifluoromethylphenyl)ethyl]imidazole
1-[3-cyano-3-(2-bromophenyl)-3-(4-chlorophenyl)propyl]-2-methylimidazole
1-[4-cyano-4-(3-cyanophenyl)-4-(2-methylphenyl)butyl]-2-chloroimidazole
1-[2-allyl-2-cyano-2-(2,4-dichlorophenyl)ethyl]imidazole
1-[2-crotyl-2-cyano-2-(2,4-dichlorophenyl)ethyl]imidazole
1-[2-methallyl-2-cyano-2-(2,4-dichlorophenyl)ethyl]imidazole
1-[2-(5-hexenyl)-2-cyano-2-(2,4-dichlorophenyl)ethyl]imidazole
1-[2-propargyl-2-cyano-2-(2,4-dichlorophenyl)ethyl]imidazole
1-[2-(4-pentynyl)-2-cyano-(2,4-dichlorophenyl)ethyl]imidazole
1-[2-(5-hexynyl)-2-cyano-(2,4-dichlorophenyl)ethyl]imidazole
1-[4-cyano-4-(2,4-dichlorophenyl)-2,2-dimethylbutyl]imidazole
1-[7-cyano-7-(2,4-dichlorophenyl)heptyl]imidazole
1-[2-cyano-2-(4-trifluoromethylphenyl)hexyl]-2-nitroimidazole
1-[2-cyano-2-(2,4-difluorophenyl)-1-(2,4-dimethylphenyl)hexyl]-2-nitroimidazole
1-[2-cyano-2-(4-iodophenyl)octyl]imidazole
1-[2-cyano-2-(3,5-dinitrophenyl)hexyl]imidazole
1-[2-cyano-2-(2,3-dimethylphenyl)hexyl]imidazole
1-[1-(n-butyl)-2-cyano-2-(2,4-dichlorophenyl)ethyl]imidazole
1-[1-(n-hexyl)-3-cyano-3-phenyl-3-(2,4-dichlorophenyl)propyl]imidazole
1-[2-phenyl-3-cyano-3-(2,4-dichlorophenyl)propyl]imidazole
1-[6-cyano-6-(4-methoxyphenyl)-6-(2-methylphenyl)hexyl]imidazole
1-[2-cyano-2-phenyl-2-(4-ethylphenyl)ethyl]imidazole
1-[2-cyano-2-(4-pyridyl)-2-phenylethyl]imidazole
1-[2-cyano-2-(4-pyrimidyl)-2-phenylethyl]imidazole
1-[2-cyano-2-(3-pyridyl)-2-phenyldecyl]imidazole
1-[10-cyano-10-(2-methoxy-4-methylphenyl)-10-phenyldecyl]imidazole
1-[2-cyano-2-(2-pyrimidyl)-2-phenylethyl]imidazole
1-[2-cyano-2-(1-naphthyl)hexyl]imidazole
1-{2-cyano-2-[1-(2,4-dichloronaphthyl)]hexyl}·imidazole
1-[1,1-tetramethylene-2-cyano-2-(2,4-dichlorophenyl)hexyl]imidazole and the acid addition salts and metal salt complexes thereof.

The arylcyanoalkyl and diarylcyanoalkylimidazoles of this invention can be prepared by various synthetic routes including the following procedures. The aralkylcyanoalkylimidazoles can be prepared by alkylating an arylacetonitrile of the formula

Z—CH$_2$CN  (III)

with an alkyl halide and sodium hydride in a solvent such as ether, tetrahydrofuran, dioxane and the like at temperatures from about 20° C. to about 100° C. to give an aralkylacetonitrile of Formula IV.

Z—CH(R$^1$)CN  (IV)

The aralkylacetonitrile (Formula IV) is hydroxyalkylated by reacting it with an aldehyde or ketone which can be straight chained, cyclized or branched in a solvent such as pyridine, N,N-dimethylformamide and the like at temperatures from about 0° C. to about 150° C. for periods from about 10 to about 40 hours to give the alcohol of Formula V.

$$Z-\underset{R^3}{\underset{|}{C(R^1)}}\underset{|}{\overset{CN}{|}}\underset{}{\overset{R_2}{|}}COH \quad (V)$$

The resultant alcohol (Formula V) is converted to the chloride via phosphorous pentachloride or thionyl chloride in a solvent such as benzene, toluene, and the like at temperatures from about 10° C. to about 110° C. The alcohol can also be converted to the methane sulfonate ester by reacting it with methane sulfonyl chloride in a solvent such as benzene, toluene and the like at temperatures from about 10° C. to about 110° C. Either the chloride or the methane sulfonate ester can be reacted with an imidazole either neat or in a solvent such as N,N-dimethylformamide, dimethylsulfoxide, diglyme and the like at temperatures from about 50° C. to about 180° C. for periods from about 10 to about 40 hours to give the desired product (Formula I) where a and b are zero.

The diarylcyanoalkylimidazoles can be prepared by reacting an arylaldehyde with an arylmagnesium halide in an anhydrous ethereal solvent such as ether, tetrahydrofuran, dioxane and the like at temperatures from about 25° C. to about 100° C. for periods from about 1 to about 24 hours to give an alcohol of Formula VI.

Z—CH(R$^1$)OH  (VI)

The alcohol (Formula VI) is converted to the halide by reacting it with phosphorous tribromide or thionyl chloride in a solvent such as benzene, toluene and the like at temperatures of from about 25° C. to about 110° C. The alcohol can also be converted to the methane sulfonate ester by reacting it with methane sulfonyl chloride in a solvent such as benzene, toluene and the like at temperatures of from about 25° C. to about 110° C. Either the halide or the methane sulfonate ester can be reacted with a metal cyanide in a solvent such as dimethylsulfoxide, N,N-dimethylformamide or the like at temperatures from about 50° C. to about 180° C. for periods from about 4 to about 24 hours to give the diarylacetonitrile of Formula VII.

Z—CH(R$^1$)CN  (VII)

The diarylacetonitrile (Formula VII) is hydroxyalkylated by reacting it with an aldehyde or ketone in a solvent such as pyridine, N,N-dimethylformamide and the like at temperatures from about 0° C. to about 150° C. for periods from about 10 to about 40 hours is to give the corresponding alcohol of Formula V. The alcohol is converted as above to the halide or methane sulfonate. Either the halide or the methane sulfonate ester can be similarly reacted as above, with an imidazole either neat or in a solvent such as N,N-dimethylformamide, dimethylsulfoxide, diglyme or the like at temperatures from about 50° C. to about 180° C. for periods from about 10 to about 40 hours to give the desired product (Formula I) where $R^1$ is aryl and a and b are zero.

The compounds of this invention can also be prepared by utilizing the procedure of Markosza and Serafin, *Roczniki Chem.*, 39, 1223 (1965); ibid. 40,1839 (1966), and Brändström and Junggren, *Tet. Letters*, 473 (1972) wherein the quaternary ammonium salt of an arylacetonitrile carbanion (formed by the action of a 25 to 50% solution of sodium hydroxide on an arylacetonitrile of Formula III followed by treatment with a quaternary ammonium halide) is extracted into an aprotic solvent such as chloroform or methylene chloride and alkylated by adding an alkyl halide to the solution to give an aralkylacetonitrile of Formula IV.

The carbanion of aralkylacetonitrile or diarylacetonitrile (Formula IV) can be bromoalkylated with a dibromo alkane under conditions similar to Markosza and Brändström to give the bromide (Formula VIII).

(VIII)

The bromide (Formula VIII) is then reacted with an imidazole either neat or in a solvent such as N,N-dimethylformamide, dimethylsulfoxide, diglyme or the like at temperatures from about 50° C. to about 180° C. for periods from about 10 to about 40 hours to give the desired product (Formula I) where $R^2$ is hydrogen and b is zero.

The carbanion of aralkylacetonitrile or diarylacetonitrile Formula IV can be bromoalkylated with a branched or aryl substituted dibromoalkane under conditions similar to Markosza and Brändström to give the bromide (Formula IX)

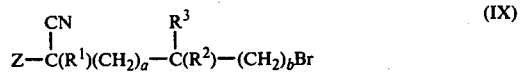

(IX)

This bromide Formula IX is then reacted with an imidazole either neat or in a solvent such as N,N-dimethylformamide, dimethylsulfoxide, diglyme or the like at temperatures from about 50° C. to about 180° C. for periods from about 10 to about 40 hours to give the desired product (Formula I).

An improved process for the preparation of the aralkylcyanoalkylimidazole of this invention involves the addition of a solution of an arylacetonitrile and an alkyl halide in dimethylsulfoxide to a 50% aqueous solution of sodium hydroxide at room temperature. To this reaction mixture is then added a dibromoalkane and the desired product (Formula VIII) is isolated in good yield. The bromide (Formula VIII) is then reacted with an imidazole either neat or with a small quantity of a high boiling solvent at temperatures from about 50° C. to about 180° C. for periods from about 10 to about 40 hours to give the desired product (Formula I).

The diarlycyanoalkylimidazoles of this invention can be similarly prepared by adding a dibromoalkane to a solution of a diarylacetonitrile in dimethylsulfoxide and 50% sodium hydroxide holding the reaction temperatures at about 20° C. to about 50° C. for periods from about 1 to about 8 hours. The resultant bromide is then converted to the imidazole via prior reaction conditions.

The acid addition salts of the arylcyanoalkyl and diarylcyanoalkylimidazoles of this invention can be prepared by adding aqueous, alcoholic or ethereal solutions of organic or mineral acids to aqueous, alcoholic or ethereal solutions of the compounds of Formula I. The resultant precipitate is then filtered washed with solvent and dried to give the desired acid addition salt. Typical acids which can be utilized in the above preparation include hydrochloric, nitric, hydrobromic, sulfuric, perchloric, phosphoric, acetic, oxalic, malic, tartaric, citric and the like.

The metal salt complexes of the arylcyanoalkyl and diarylcyanoalkylimidazoles of this invention can be prepared by treating an aqueous or alcoholic solution of a compound of Formula I or its acid addition salt with an aqueous or alcoholic solution of a metal salt. The precipitate is filtered, washed with solvent and dried to give the desired metal salt complex (Formula II).

The metal salts that can be utilized in the above procedure include those which are formed by the combination of a metal cation such as Mg, Ca, Ba, Sn, Pb, Cu, Zn, Cd, Cr, Mn, Fe, Co, Ni and the like and an anion such as chloride, bromide, iodide, sulfate, bisulfate, phosphate, nitrate, perchlorate, carbonate, bicarbonate, hydrosulfide, hydroxide, acetate, oxalate, malate, citrate, tartarate and the like.

The metal salt complex can also be prepared by mixing stoichiometric or excess amounts of the metal salt and an aralkyl or diarylcyano alkyl imidazole in the desired amount of solvent containing the appropriate adjuvants just prior to spraying the plants. Adjuvants that may be included in this "in-situ" preparation may be detergents, emulsifiers, wetting agents, spreading agents, dispersing agents, stickers, adhesives, and the like which are used in agricultural applications. The metal salt complexes of the compounds of this invention provide a safening effect which reduces the phytotoxicity while retaining their fungicidal efficacy.

It has also been found that metal containing fungicides can also act as safening agents when used in place of metal salts. Typical metal containing fungicides that can be utilized in these procedures are:

a. Dithiocarbamates and derivatives such as: ferric dimethyldithiocarbamate (ferbam), zinc dimethyldithiocarbamate (ziram), manganese ethylenebisdithiocarbamate (maneb) and its coodination product with zinc ion (mancozeb), zinc ethylenebisdithiocarbamate (zineb);

b. Copper-based fungicides such as: cuprous oxide, copper naphthenate, and Bordeaux mixture; and c. Miscellaneous fungicides such as: phenylmercuric acetate N-ethylmercuri-1,2,3,6-tetrahydro-3,6-endomethano-3,4,5,6,7,7-hexachlorophthalimide, phenylmercuric monoethanolammonium lactate, nickel-containing compounds and calcium cyanamide.

Solvents that can be utilized in the above procedures include any polar solvent e.g., water, methanol, ethanol, isopropanol or ethylene glycol and any aprotic dipolar solvent e.g., dimethylsulfoxide, acetonitrile, dimethylformamide, nitromethane or acetone.

The following examples are provided to demonstrate to one skilled in the art a method of preparation of the arylcyanoalkyl and diarylcyanoalkylimidazoles their acid addition salts and metal salt complexes. These examples are provided merely as illustrations and are not to be considered as limitations or restrictions of the scope of this invention.

EXAMPLE 15

1-[2-cyano-2-(2,4-dichlorophenyl)hexyl]imidazole hydrochloride (a) α-n-butyl-2,4-dichlorobenzyl cyanide Sodium hydride (0.3 mole as a 50% dispersion in mineral oil) is washed with 100 ml. of dry n-hexane to remove the mineral oil, then blanketed with dry nitrogen and suspended in 250 ml. of freshly distilled tetrahydrofuran. To this sodium hydride suspension is added dropwise at room temperature, a solution of 2,4-dichlorobenzyl cyanide (55.8g., 0.3 mole) dissolved in 100 ml. of tetrahydrofuran. When the addition is completed, the temperature is maintained at 30° C. for an additional 0.5 hours. A solution of n-butyl iodide is then added dropwise and the resultant reaction mixture is stirred at 40° C. overnight under nitrogen. The reaction mixture is poured into 1 liter of water and extracted with (3 × 200 ml.) of ether. The combined ether extracts are washed with water, dilute hydrochloric acid, saturated sodium bicarbonate solution, saturated sodium chloride solution and dried over magnesium sulfate. The solvent is evaporated to give 71g. of a brown crude product which is further purified by vacuum distillation (105°–7°/0.1 mm) to give 61.7g. (85%) of product, which is identified by nmr.

(b) 2-cyano-2-(2,4-dichlorophenyl)hexan-1-ol

To an ice cold stirred solution of α-n-butyl-2,4-dichlorobenzylcyanide (5g., 0.02 mole) in 20 ml. of pyridine containing a suspension of paraformaldehyde (2.4g., 0.08 mole) is added 1 ml. of benzyl triethylammonium hydroxide. The mixture is stirred under nitrogen at room temperature for 16 hours. The reaction mixture is poured into 300 ml. of water and extracted with ether. The combined ether extracts are washed with water, saturated sodium chloride solution and dried over magnesium sulfate. The solvent is evaporated to give 5.6g. of a thick oil, which is identified by nmr.

(c) 2-cyano-2-(2,4-dichlorophenyl)hexyl methane sulfonate

A mixture of 2-cyano-2-(2,4-dichlorophenyl)hexan-1-ol (5.6g., 0.02 mole) and methane sulfonyl chloride (2.9g., 0.025 mole) in 200 ml. of benzene is added dropwise at 10° C., 2.8g. (0.027) of triethylamine. The reaction mixture is stirred at room temperature for 30 minutes and then heated on a steam bath for another 30 minutes. The precipitate formed is filtered and the filtrate is washed with dilute hydrochloric acid, water, saturated sodium bicarbonate solution, saturated sodium chloride solution and dried over magnesium sulfate. The solvent is evaporated to give 6.3g. of product.

(d) 1-[2-cyano-2-(2,4-dichlorophenyl)hexyl]imidazole hydrochloride

A mixture of 2-cyano-2-(2,4-dichlorophenyl)hexyl methane sulfonate (100g., 0.29 mole), imidazole (100g., 1.5 mole) and N,N-dimethylformamide (5 ml.) is heated with stirring at 135° C. overnight. The reaction mixture is poured into water and extracted with ether. The combined ether extracts are dried over magnesium sulfate. The drying agent is filtered and into the ethereal solution is bubbled dry hydrogen chloride gas. The white solid which precipitates is collected and dried to give 70.4g. (68%) of the expected product, which is identified by nmr.

EXAMPLE 24

Zinc Chloride Complex of 1-[2-cyano-2,4-dichlorophenyl)hexyl]imidazole

To an ethanolic solution of 1-[2-cyano-2-(2,4-dichlorophenyl)hexyl]imidazole (3g., 0.01 mole) is added a solution of zinc chloride (0.63g., 0.01 mole) dissolved in 10 ml. of absolute ethanol. The white precipitate which is formed is filtered, washed with ethanol and dried to give 3.1g. of desired product; mp 196°–198° C., which is identified by nmr.

EXAMPLE 31

1-[2-cyano-2-(2,4-dichlorophenyl)decyl]imidazole hydrochloride (a) α-n-octyl-2,4-dichlorobenzyl cyanide Sodium hydride (0.13 moles as a 50% dispersion in mineral oil) is washed with 100 ml. of dry n-hexane to remove the mineral oil, then blanketed with dry nitrogen and suspended in 250 ml. of freshly distilled tetrahydrofuran. To this sodium hydride suspension is added dropwise at room temperature, a solution of 2,4-dichlorobenzyl cyanide (25g., 0.13 mole) dissolved in 100 ml. of tetrahydrofuran. When the addition is completed the temperature is maintained at 30° C. for an additional 0.5 hours. A solution of n-octylbromide (27g., 0.14 mole) is then added dropwise and the resultant reaction mixture is stirred at 40° C. overnight under nitrogen. The reaction mixture is poured into 1 liter of water and extracted with (3 × 200 ml.) of ether. The combined ether extracts are washed, with water, dilute hydrochloric acid, saturated sodium, bicarbonate solution saturated sodium chloride solution, and dried over magnesium sulfate. The solvent is evaporated to give 39.8g. (100%) of product.

(b) 2-cyano-2-(2,4-dichlorophenyl)decan-1-ol

To an ice cold stirred solution of α-n-octyl-2,4-dichlorobenzyl cyanide (40g., 0.14 mole) in 250 ml. of pyridine containing a suspension of paraformaldehyde (21g., 0.7 mole) is added 1 ml. of benzyl triethylammonium hydroxide. The mixture is stirred under nitrogen at room temperature for 72 hours. The reaction mixture is poured into 2 liters of water and extracted with ether. The combined ether extracts are washed with water, saturated sodium chloride solution and dried over magnesium sulfate. The solvent is evaporated to give 40g. of a thick oil.

(c) 2-cyano-2-(2,4-dichlorophenyl)decyl methane sulfonat

To a mixture of 2-cyano-2-(2,4-dichlorophenyl)decan-1-ol (40g., 0.12 mole) and methane sulfonyl chloride (15.3g., 0.13 mole) in 2 liters of benzene is added dropwise at 10° C., 14.8g., (0.14 mole) of triethylamine. The reaction mixture is stirred at room temperature for 30 minutes and then heated on a steam bath for another 30 minutes. The precipitate formed is filtered and the filtrate is washed with dilute hydrochloric acid, water, saturated sodium bicarbonate solution, saturated sodium chloride solution and dried over magnesium sulfate. The solvent is evaporated to give 41.3g. of product, which is identified by nmr.

(d) 1-[2-cyano-2-(2,4-dichlorophenyl) decyl]imidazole hydrochloride

A mixture of 2-cyano-2-(2,4-dichlorophenyl) decyl methane sulfonate (41.3g., 0.1 mole), imidazole (27.7g., 0.4 mole) and N,N-dimethylformamide (1.5 ml.) is heated with stirring at 130° C. for 24 hours. The reaction mixture is poured into water and extracted with ether. The combined ether extracts are washed with water and dried over sodium sulfate. Into the etheral solution is bubbled dry hydrogen chloride gas. The white solid which precipitates is collected and dried to give 11.7g. (28%) of the expected product, which is identified by nmr.

EXAMPLE 27

1-[2-cyano-2-(4-chlorophenyl)propyl]imidazole hydrochloride

(a) 2-cyano-2-(4-chlorophenyl)propan-1-ol

To an ice cold stirred solution of α-methyl-4-chlorobenzyl cyanide* (50g., 0.3 mole) in 500 ml. of pyridine containing a suspension of paraformaldehyde (36g., 1.2 mole) is added 1 ml. of benzyl triethylammonium hydroxide. The mixture is stirred under nitrogen at room temperature for 72 hours. The reaction mixture is poured into water and extracted with ether. The combined ether extracts are washed with water, saturated sodium chloride solution and dried over magnesium sulfate. The solvent is evaporated to give a thick oil, 58.4g., which is identified by nmr.

*  - Commercially available

(b) 2-cyano-2-(4-chlorophenyl)propyl methane sulfonate to a mixture of 2-cyano-2-(4-chlorophenyl)propan-1-ol (68g., 0.3 mole) and methane sulfonyl chloride (37.5g., 0.33 mole) in 2 liters of benzene is added dropwise at 10° C., 36g., (0.36 mole) of triethylamine. The reaction mixture is stirred at room temperature for 30 minutes and then heated on a steam bath for another 30 minutes. The precipitate formed is filtered and the filtrate is washed with dilute hydrochloric acid, water, saturated sodium bicarbonate solution, saturated sodium chloride solution and dried over magnesium sulfate. The solvent is evaporated to give 63g. of product.

(c) 1-[2-cyano-2-(4-chlorophenyl)propyl]imidazole-hydrochloride

A mixture of 2-cyano-2-(4-chlorophenyl)propyl methane sulfonate (63g., 0.23 mole), imidazole (62.6g., 0.9 mole) and N,N-dimethylformamide (3 ml.) is heated with stirring at 130° C. for 24 hours. The reaction mixture is poured into water and extracted with ether. The combined ether extracts are washed with water and dried over magnesium sulfate. Into the ethereal solution is bubbled dry hydrogen chloride gas. The white solid which precipitate is collected and dried to give 38g. (58.6%) of the expected product, which is identified by nmr.

EXAMPLE 28

1-[2-cyano-2-(2-chlorophenyl)-2-(4-chlorophenyl)ethyl]imidazolium nitrate

(a) 2,4'-dichlorobenzhydrol

To 12.7g. (0.52 moles) of magnesium turnings in 200 ml. of anhydrous ether is added 10.0g. (0.052 moles) of p-bromochlorobenzene, and the mixture is warmed to reflux. When the Grignard reaction begins, the heat is removed and 80.0g. (0.47 moles) of additional p-bromochlorobenzene in 80 ml. of ether is added dropwise as the refluxing continues. When the addition is completed, the reaction is heated at reflux for 2 hours, cooled, and 73.4g. (0.52 moles) of o-chlorobenzaldehyde are slowly added. The reaction is refluxed for 2 hours, cooled and poured into iced water. The resulting mixture is made acidic with hydrochloric acid, and the organic phase is separated. The aqueous layer is extracted with ether, and the extract is added to the organic phase. This solution is washed with water, dried over anhydrous magnesium sulfate and concentrated to give an oily solid. The material is crystallized from petroleum ether to give 109.4g. (83%) of the product, mp 68°-70°.

(b) 2,4'-dichlorodiphenyl bromomethane

To 109.4g. (0.432 moles) of 2,4'-dichlorobenzyhydrol in 125 ml. of benzene is slowly added 68.4g. (0.253 moles) of phosphorus tribromide at 10° C. When the addition is complete the reaction is stirred for 2 hours. The benzene is then stripped off at atmospheric pressure with the pot temperature reaching 115° C. The reaction is cooled, and poured into iced water. After stirring for 15 minutes, the organic material is extracted out with ether (3 × 100 ml.). The extracts are combined, washed with brine, dried over anhydrous magnesium sulfate and then concentrated to give 116.5g. of the crude product. A distillation gives 97.2g. (69%) of the pure bromomethane product (140°-5° C./0.1 mm).

(c) 2,4'-dichlorodiphenylacetonitrile

To 85.0g. (0.27 moles) of the prepared bromomethane derivatives is added at 125° C., 25.5g. (0.285 moles) of anhydrous cuprous cyanide. The temperature gradually exothermed to 140° C. before it is cooled back to 125° C. After stirring for 1 hour at 125° C., the reaction is heated up to 150° C. for an additional hour. The reaction is cooled and mixed with 200 ml. of benzene. The insoluble solid is filtered, and the filtrate is stripped to dryness giving 70.6g. of the crude product. A distillation provided 63.3g. (90%) of the acetonitrile derivative (140°-4° C./0.1 mm.).

(d) 2-cyano-2-(2-chlorophenyl)-2-(4-chlorophenyl)ethanol

To an ice cold stirred solution of 2,4'-dichlorodiphenylacetonitrile (20g., 0.08 mole) in 100 ml. of pyridine containing a suspension of paraformaldehyde (9.2g., 0.3 mole) is added 1 ml. of benzyl triethylammonium hydroxide. The mixture is stirred under nitrogen at room temperature for 60 hours. The reaction mixture is poured into 1.5 liters of water and extracted with ether. The combined ether extracts are washed with water, saturated sodium chloride solution and dried over magnesium sulfate. The solvent is evaporated to give 18g. of a thick oil, which is identified by nmr.

(e) 2-cyano-2-(2-chlorophenyl)-2-(4-chlorophenyl)ethyl methane sulfonate

To a mixture of 2-cyano-2-(2-chlorophenyl)-2-(4-chlorophenyl)ethanol (18g., 0.06 mole) and methane sulfonyl chloride (7.8g., 0.07 mole) in 200 ml. of benzene is added dropwise at 10° C., 7.5g. (0.08 mole) of triethylamine. The reaction mixture is stirred at room temperature for 30 minutes and then heated on a steam bath for another 30 minutes. The precipitate formed is filtered and the filtrate is washed with dilute hydrochloric acid, water, saturated sodium bicarbonate solution, saturated sodium chloride solution and dried over magnesium sulfate. The solvent is evaporated to give 22g. of product; mp 214°–7° C., which is identified by nmr.

(f) 1-[2-cyano-2-(2-chlorophenyl)-2-(4-chlorophenylethyl]imidazolium nitrate

A mixture of 2-cyano-2-(2-chlorophenyl)-2-(4-chlorophenyl)ethyl methane sulfonate (22g., 0.06 mole), imidazole (16.3g., 0.24 mole) and N,N-dimethylformamide (1 ml.) is heated with stirring at 150° C. for 24 hours. The reaction mixture is poured into water and extracted with ether. The combined ether extracts are washed with water and dried over magnesium sulfate. Into the ethereal solution is poured with, rigorous stirring, an excess of concentrated nitric acid solution. The resultant precipitate is filtered and washed with ether and dried to give 10.8g. (44.4%) of product, which is identified by nmr.

EXAMPLE 41

1-[2-cyano-2-(2,4-dichlorophenyl)-4-phenyl butyl]imidazolium nitrate (a) α-phenethyl-2,4-dichlorobenzyl cyanide Sodium hydride (0.13 mole as a 50% dispersion in mineral oil) is washed with 100 ml. of dry n-hexane to remove the mineral oil, then blanketed with dry nitrogen and suspended in 250 ml. of freshly distilled tetrahydrofuran. To this sodium hydride suspension is added dropwise at room temperature a solution of 2,4-dichlorobenzyl cyanide (25g., 0.13 mole) dissolved in 100 ml. of tetrahydrofuran. When the addition is completed, the temperature is maintained at 30° C. for an additional 0.5 hours. A solution of phenethylbromide (26g., 0.14 mole) is then added dropwise and the resultant reaction mixture is stirred at 40° C. overnight under nitrogen. The reaction mixture is poured into 1 liter of water and extracted with (3 × 200 ml.) of ether. The combined ether extracts are washed with water, dilute hydrochloric acid, saturated sodium bicarbonate solution, saturated sodium chloride solution and dried over magnesium sulfate. The solvent is evaporated and the crude product distilled (144°–56°/0.03 mm) to give 26.6g. (70.5%) of product, which is identified by nmr.

(b) 2-cyano-2-(2,4-dichlorophenyl)-4-phenyl butan-1-ol

To an ice cold stirred solution of α-phenethyl-2,4-dichlorobenzyl cyanide (26.5g., 0.09 mole) in 200 ml. of pyridine containing a suspension of paraformaldehyde (11g., 0.35 mole) is added 1 ml. of benzyl triethylammonium hydroxide. The mixture is stirred under nitrogen at room temperature for 24 hours. The reaction mixture is poured into 1 liter of water and extracted with ether. The combined ether extracts are washed with water, saturated sodium chloride solution and dried over magnesium sulfate. The solvent is evaporated to give 25.4g. of a thick oil, which is identified by nmr.

(c) 2-cyano-2-(2,4-dichlorophenyl)-4-phenyl butyl methane sulfonate

To a mixture of 2-cyano-2-(2,4-dichlorophenyl)-4-phenyl butan-1-ol (25.4g., 0.08 mole) and methane sulfonyl chloride (10g., 0.09 mole) in 1 liter of benzene is added dropwise at 10° C., 9.6g., (0.09 mole) of triethylamine. The reaction mixture is stirred at room temperature for 30 minutes and then heated on a steam bath for another 30 minutes. The precipitate formed is filtered and the filtrate is washed with dilute hydrochloric acid, water, saturated sodium bicarbonate solution, saturated sodium chloride solution and dried over magnesium sulfate. The solvent is evaporated to give 25.1g. of product, which is identified by nmr.

(d) 1-[2-cyano-2-(2,4-dichlorophenyl)-4-phenyl butyl]imidazolium nitrate

A mixture of 2-cyano-2-(2,4-dichlorophenyl)-4-phenyl butyl methane sulfonate (25g., 0.063 mole), imidazole (17g., 0.25 mole) and N,N-dimethylformamide (1 ml.) is heated with stirring at 150° C. for 24 hours. The reaction mixture is poured into water and extracted with ether. The combined ether extracts are washed with water and dried over magnesium sulfate. Into the ethereal solution is poured, with rigorous stirring, an excess of concentrated nitric acid solution. The resultant precipitate is filtered and washed with ether and dried to give 17.5g. (64%) of product, which is identified by nmr.

EXAMPLE 37

1-[2-cyano-2-(2-pyridyl)-2-phenylethyl]imidazole (a) 2-cyano-2-(2-pyridyl)-2-phenyl ethanol To an ice cold stirred solution of phenyl-2-pyridyl acetonitrile* (50g., 0.26 mole) in 350 ml. of pyridine containing a suspension of paraformaledhyde (31g., 1.0 mole) is added 1 ml. of benzyl triethylammonium hydroxide. The mixture is stirred under nitrogen at room temperature for 24 hours. The reaction mixture is poured into water and extracted with ether. The combined ether extracts are washed with water, saturated sodium chloride solution and dried over magnesium sulfate. The solvent is evaporated to give a thick oil 58g., which is identified by nmr.
*Commercially available (b) 2-cyano-2-(2-pyridyl)-2-phenyl ethyl methane sulfonate To a mixture of 2-cyano-2-(2-pyridyl)-2-phenyl ethanol (25g., 0.1 mole) and methane sulfonyl chloride (14g., 0.11 mole) in 600 ml. of benzene is added dropwise at 10° C., 13.5g. (0.12 mole) of triethylamine. The reaction mixture is stirred at room temperature for 30 minutes and then heated on on a steam bath for another 30 minutes. The precipitate formed is filtered and the filtrate is washed with dilute hydrochloric acid, water, saturated sodium bicarbonate solution, saturated sodium chloride solution and dried over magnesium sulfate. The solvent is evaporated to give 19.5g. of product; mp 83°–5° C. which is identified by nmr.

(c) 1-[2-cyano-2-(2-pyridyl)-2-phenylethyl]imidazole

A mixture of 2-cyano-2-(2-pyridyl)-2-phenyl ethyl methane sulfonate (11g., 0.037 mole), imidazole (10g., 0.15 mole) and N,N-dimethylformamide (1 ml.) is heated with stirring at 140° C. for 24 hours. The reaction mixture is poured into water and extracted with ether. The combined ether extracts are washed with water and dried over sodium sulfate. When the solvent is evaporated, a total of 3.5g. (34%) of product is obtained, which is identified by nmr.

EXAMPLE 48

1-[6-cyano-6-(2,4-dichlorophenyl)decyl]imidazole (a) α-n-butyl-2,4-dichlorobenzyl cyanide This compound is prepared in Example 2a.

(b) 6-cyano-6-(2,4-dichlorophenyl)decyl bromide

To 30 ml. of 50% sodium hydroxide solution containing 1g. of benzyl triethylammonium chloride is added dropwise at room temperature, a mixture of 11g. (0.045 mole) of α-n-butyl benzyl cyanide and 13.6g. (0.6 mole) of 1,5-dibromobutane. The mixture is heated to 80° C. with rigorous stirring overnight. It is then poured into water and extracted with ether. The combined ether extracts are washed with water and dried over magnesium sulfate. Solvent is evaporated and the unreacted 1,5-dibromobutane is removed under vacuum to give 14.2g. of product, which is identified by nmr.

(c) 1-[6-cyano-6-(2,4-dichlorophenyl)decyl]imidazole

A mixture of 6-cyano-6-(2,4-dichlorophenyl)decyl bromide (14.2g., 0.036 mole) imidazole (10g., 0.15 mole) and 5 ml. N,N-dimethylformamide is heated at 120° C. for 24 hours. The reaction mixture is poured into water and extracted with ether. The combined ether extracts are dried over magnesium sulfate and filtered. Into the ethereal solution is bubbled dry hydrogen chloride gas until no more oily precipitate forms. The solvent is then decanted and the oily residue is taken up in acetone and neutralized with dilute ammonium hydroxide solution. The purified free base is extracted into ether and dried over magnesium sulfate. When the solvent is evaporated, a total of 6.5g. (47.8%) of product is obtained, which is identified by nmr.

In Table I a number of the more representative compounds of this invention are presented, their melting points and elemental analysis have been provided in Table II. These tables are also to merely illustrate representative compounds of this invention and should not be considered as limitations or restrictions of the scope of this invention.

TABLE I $$Z-\underset{R^1}{\underset{|}{\overset{CN}{\overset{|}{C}}}}-(CH_2)_a-\underset{R^2}{\underset{|}{\overset{R^3}{\overset{|}{C}}}}-(CH_2)_b-N\underset{\diagdown\diagup}{\diagup\!\!\!=\!\!\!\diagdown}-(X)_c \cdot M$$

| Example No. | Z | $R^1$ | $R^2$ | $R^3$ | a | b | $(X)_c \cdot M$ |
|---|---|---|---|---|---|---|---|
| 1 | $C_6H_5$ | $C_4H_9n$ | H | H | 0 | 0 | — |
| 2 | $C_6H_5$ | $C_4H_9n$ | H | H | 0 | 0 | —HCl |
| 3 | $2\text{-}CH_3C_6H_4$ | $C_4H_9n$ | H | H | 0 | 0 | —$HNO_3$ |
| 4 | $3\text{-}CH_3C_6H_4$ | $C_4H_9n$ | H | H | 0 | 0 | —HCl |
| 5 | $4\text{-}CH_3C_6H_4$ | $C_4H_9n$ | H | H | 0 | 0 | —HCl |
| 6 | $4\text{-}BrC_6H_4$ | $C_4H_9n$ | H | H | 0 | 0 | —$HNO_3$ |
| 7 | $4\text{-}FC_6H_4$ | $C_4H_9n$ | H | H | 0 | 0 | —HCl |
| 8 | $3\text{-}CF_3C_6H_4$ | $C_4H_9n$ | H | H | 0 | 0 | — |
| 9 | $4\text{-}C_6H_5C_6H_4$ | $C_4H_9n$ | H | H | 0 | 0 | — |
| 10 | $4\text{-}tC_4H_9C_6H_4$ | $C_4H_9n$ | H | H | 0 | 0 | —HCl |
| 11 | $4\text{-}CH_3OC_6H_4$ | $C_4H_9n$ | H | H | 0 | 0 | —HCl |
| 12 | $4\text{-}NO_2C_6H_4$ | $C_4H_9n$ | H | H | 0 | 0 | —HCl |
| 13 | $4\text{-}C_6H_5COC_6H_4$ | $C_4H_9n$ | H | H | 0 | 0 | — |
| 14 | $2,4\text{-}ClC_6H_3$ | $C_4H_9n$ | H | H | 0 | 0 | — |
| 15 | $2,4\text{-}ClC_6H_3$ | $C_4H_9n$ | H | H | 0 | 0 | —HCl |
| 16 | $2,6\text{-}ClC_6H_3$ | $C_4H_9n$ | H | H | 0 | 0 | —$HNO_3$ |
| 17 | $2,4\text{-}CH_3C_6H_3$ | $C_4H_9n$ | H | H | 0 | 0 | —$HNO_3$ |
| 18 | $3,4,5\text{-}CH_3OC_6H_2$ | $C_4H_9n$ | H | H | 0 | 0 | — |
| 19 | (benzodioxole) | $C_4H_9n$ | H | H | 0 | 0 | —HCl |
| 20 | (naphthyl) | $C_4H_9n$ | H | H | 0 | 0 | — |
| 21 | $Z + R^1 =$ (fluorene) | | H | H | 0 | 0 | —HCl |
| 22 | (thienyl) | $C_4H_9n$ | H | H | 0 | 0 | —$HNO_3$ |
| 23 | (pyridyl) | $C_4H_9n$ | H | H | 0 | 0 | — |
| 24 | $2,4\ ClC_6H_3$ | $C_4H_9n$ | H | H | 0 | 0 | —½ $ZnCl_2$ |
| 25 | $C_6H_5$ | $CH_3$ | H | H | 0 | 0 | —HCl |
| 26 | $C_6H_5$ | $C_6H_5$ | H | H | 0 | 0 | —HCl |
| 27 | $4\text{-}ClC_6H_4$ | $CH_3$ | H | H | 0 | 0 | —HCl |
| 28 | $4\text{-}ClC_6H_4$ | $2\text{-}ClC_6H_4$ | H | H | 0 | 0 | —$HNO_3$ |
| 29 | $4\text{-}ClC_6H_4$ | $4\text{-}ClC_6H_4$ | H | H | 0 | 0 | —$HNO_3$ |
| 30 | $2,4\text{-}ClC_6H_3$ | H | H | H | 0 | 0 | —HCl |

TABLE I-continued $$Z-\underset{R^1}{\underset{|}{\overset{CN}{\overset{|}{C}}}}-(CH_2)_a-\underset{R^2}{\underset{|}{\overset{R^3}{\overset{|}{C}}}}-(CH_2)_b-N\diagdown\diagup(X)_c \cdot M$$

| Example No. | Z | R¹ | R² | R³ | a | b | (X)$_c$ · M |
|---|---|---|---|---|---|---|---|
| 31 | 2,4-ClC₆H₃ | C₈H₁₇n | H | H | 0 | 0 | —HCl |
| 32 | 2,4-ClC₆H₃ | 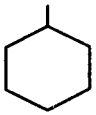 | H | H | 0 | 0 | — |
| 33 | 2,4-ClC₆H₃ | 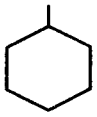 | H | H | 0 | 0 | —HCl |
| 34 | 2,4-ClC₆H₃ | 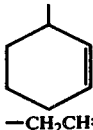 | H | H | 0 | 0 | — |
| 35 | 2,4-ClC₆H₃ | —CH₂CH=CH₂ | H | H | 0 | 0 | —HNO₃ |
| 36 | 2,4-ClC₆H₃ | —CH₂C≡CH | H | H | 0 | 0 | —HNO₃ |
| 37 | 2,4-ClC₆H₃ |  | H | H | 0 | 0 | — |
| 38 | 2,4-ClC₆H₃ | C₆H₅ | H | H | 0 | 0 | —HNO₃ |
| 39 | 2,4-ClC₆H₃ | —CH₂C₆H₅ | H | H | 0 | 0 | —HNO₃ |
| 40 | 2,4-ClC₆H₃ |  | H | H | 0 | 0 | — |
| 41 | 2,4-ClC₆H₃ | —CH₂CH₂C₆H₅ | H | H | 0 | 0 | —HNO₃ |
| 42 | 2,4-ClC₆H₃ | 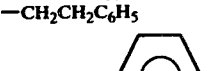 | H | H | 0 | 0 | — |
| 43 | 2,4-ClC₆H₃ |  | H | H | 0 | 0 | —HNO₃ |
| 44 | 2,4-ClC₆H₃ | H | H | H | 2(1) | 0(1) | — |
| 45 | 2,4-ClC₆H₃ | C₄H₉n | H | H | 1 | 0 | —HCl |
| 46 | 2,4-ClC₆H₃ | C₄H₉n | H | H | 2(1) | 0(1) | — |
| 47 | 2,4-ClC₆H₃ | C₄H₉n | H | H | 3(2) | 0(1) | — |
| 48 | 2,4-ClC₆H₃ | C₄H₉n | H | H | 4(2) | 0(2) | — |
| 49 | 2,4-ClC₆H₃ | H | H | C₃H₇n | 0 | 0 | — |
| 50 | 2,4-ClC₆H₃ | C₄H₉n | C₆H₅ | H | 0 | 0 | — |
| 51 | 4-ClC₆H₄ | CH₃ | C₆H₅ | H | 0 | 0 | — |
| 52 | 2,4-ClC₆H₃ | C₄H₉n | H | H | 0 | 0 | 4,5-Cl— |
| 53 | C₆H₅ | C₄H₉n | H | H | 0 | 0 | 2-CH₃ · HNO₃ |
| 54 | 2,4-ClC₆H₃ | C₄H₉n | H | H | 0 | 0 | —HClO₄ |
| 55 | 2,4-ClC₆H₃ | C₄H₉n | H | H | 0 | 0 | —(COOH)₂ |
| 56 | C₆H₅ | C₄H₉n | H | H | 0 | 0 | —(COOH)₂ |
| 57 | C₆H₅ | C₄H₉n | H | H | 0 | 0 | 4-NO₂— |
| 58 | C₆H₅ | C₆H₅ | C₆H₅ | H | 0 | 0 | — |

TABLE II

| Ex. No. | M.P. | C Theory | C Found | H Theory | H Found | Halogen Theory | Halogen Found | N Theory | N Found | O Theory | O Found | S Theory | S Found | Metal Theory | Metal Found |
|---|---|---|---|---|---|---|---|---|---|---|---|---|---|---|---|
| 1 | oil | 75.86 | 73.66 | 7.56 | 7.50 | | | 16.59 | 16.17 | | | | | | |
| 2 | 160-2 | 66.31 | 65.26 | 6.96 | 6.77 | 12.23 | 12.34 | 14.50 | 14.47 | | | | | | |
| 3 | 125-127 | 61.80 | 62.10 | 6.71 | 6.73 | | | 16.96 | 17.13 | 14.53 | 14.10 | | | | |
| 4 | 165-7 | 67.20 | 66.49 | 7.30 | 7.34 | 11.67 | 11.31 | 13.83 | 13.54 | | | | | | |
| 5 | 165-8 | 67.20 | 64.44 | 7.30 | 7.31 | 11.67 | 11.38 | 13.83 | 13.23 | | | | | | |
| 6 | 136-8 | 48.62 | 48.92 | 4.84 | 5.00 | 20.22 | 20.35 | 14.17 | 14.03 | 12.14 | 11.87 | | | F 6.17/6.8 | |
| 7 | 172-4 | 62.43 | 61.84 | 6.22 | 6.36 | 11.51 | 11.58 | 13.65 | 13.63 | | | | | | |
| 8 | oil | 63.54 | 63.02 | 5.65 | 5.38 | 17.74 | 18.87 | 13.08 | 11.86 | | | | | | |
| 9 | 43-5 | 80.20 | 78.43 | 7.04 | 7.10 | | | 12.75 | 11.69 | | | | | | |
| 10 | 212-4 | 69.44 | 66.05 | 8.16 | 8.31 | 10.25 | 10.10 | 12.15 | 11.51 | | | | | | |
| 11 | 122-6 | 63.85 | 62.13 | 6.93 | 6.54 | 11.09 | 10.86 | 13.14 | 12.33 | 4.98 | 7.60 | | | | |
| 12 | 113-5 | 57.40 | 54.09 | 5.72 | 5.86 | 10.59 | 10.94 | 16.73 | 15.96 | 9.56 | 13.00 | | | | |
| 13 | 40-5 | 77.30 | 76.68 | 6.49 | 6.90 | | | 11.76 | 10.55 | 4.46 | 6.64 | | | | |
| 14 | 83-5 | 59.63 | 59.42 | 5.31 | 5.16 | 22.00 | 21.94 | 13.04 | 12.96 | | | | | | |

TABLE II-continued

| Ex. No. | M.P. | C Theory | C Found | H Theory | H Found | Halogen Theory | Halogen Found | N Theory | N Found | O Theory | O Found | S Theory | S Found | Metal Theory | Metal Found |
|---|---|---|---|---|---|---|---|---|---|---|---|---|---|---|---|
| 15 | 170-2 | 53.38 | 53.35 | 5.06 | 5.05 | 29.65 | 29.92 | 11.71 | 11.52 | | | | | | |
| 16 | 141-3 | 49.88 | 49.55 | 4.17 | 4.63 | 18.41 | 18.75 | 14.54 | 14.34 | 12.46 | 12.71 | | | | |
| 17 | 148-150 | 62.77 | 63.12 | 7.02 | 7.01 | | | 16.27 | 16.17 | 13.94 | 14.20 | | | | |
| 18 | oil | 66.45 | 65.32 | 7.33 | 7.45 | | | 12.23 | 11.83 | 13.97 | 15.77 | | | | |
| 19 | 210-212 | 61.17 | 60.40 | 6.04 | 5.92 | 10.62 | 10.39 | 12.58 | 13.44 | 9.58 | 10.18 | | | | |
| 20 | oil | 79.17 | 77.76 | 6.98 | 7.20 | | | 13.85 | 13.23 | | | | | | |
| 21 | 250(dec) | 70.24 | 67.40 | 4.59 | 4.82 | 11.52 | 10.71 | 13.65 | 12.55 | | | | | | |
| 22 | 93-7 | 52.16 | 52.58 | 5.62 | 5.71 | | | 17.37 | 17.17 | 14.88 | 15.07 | 9.94 | 10.40 | | |
| 23 | oil | 70.83 | 68.32 | 7.13 | 6.98 | | | 20.02 | 20.63 | | | | | 8.31 | 8.80 |
| 24 | 196-8 | 49.22 | 48.91 | 4.38 | 4.22 | 27.24 | 26.84 | 10.76 | 10.86 | | | | | | |
| 25 | 223-5 | 69.79 | 68.54 | 5.21 | 5.11 | 11.44 | 12.40 | 13.56 | 13.27 | | | | | | |
| 26 | 231-6 | 63.03 | 62.75 | 5.70 | 5.85 | 14.31 | 14.48 | 16.96 | 16.81 | | | | | | |
| 27 | 212-4 | 55.31 | 54.74 | 4.64 | 4.58 | 25.11 | 25.45 | 14.88 | 15.35 | | | | | | |
| 28 | 170-3 | 53.35 | 52.00 | 3.48 | 3.65 | 17.50 | 17.85 | 13.83 | 10.90 | 11.84 | 12.74 | | | | |
| 29 | 192-4 | 53.35 | 53.51 | 3.48 | 3.76 | 17.50 | 17.28 | 13.83 | 13.21 | 11.84 | 12.27 | | | | |
| 30 | 157-9 | 47.63 | 45.58 | 3.33 | 3.95 | 35.15 | 33.37 | 13.89 | 12.99 | | | | | | |
| 31 | 139-141 | 57.91 | 57.86 | 6.31 | 6.24 | 25.64 | 25.34 | 10.12 | 9.96 | | | | | | |
| 32 | 137-9 | 62.07 | 62.31 | 5.50 | 20.36 | 20.24 | 12.07 | 12.12 | | | | | | | |
| 33 | >250 | 56.19 | 56.19 | 5.24 | 5.40 | 27.65 | 27.26 | 10.92 | 11.08 | | | | | | |
| 34 | 55-7 | 62.44 | 61.61 | 4.95 | 5.01 | 20.48 | 20.23 | 12.14 | 11.99 | | | | | | |
| 35 | 154-6 | 48.79 | 48.89 | 3.82 | 3.96 | 19.20 | 19.86 | 15.17 | 14.59 | 13.00 | 12.55 | | | | |
| 36 | 149-152 | 49.06 | 47.59 | 3.29 | 3.21 | 19.31 | 19.23 | 15.26 | 15.40 | 13.07 | 13.41 | | | | |
| 37 | oil | 74.43 | 72.36 | 5.14 | 5.14 | | | 20.42 | 20.11 | | | | | | |
| 38 | 160-3 | 53.35 | 52.19 | 3.48 | 3.51 | 17.50 | 17.83 | 13.83 | 12.93 | 11.84 | 12.07 | | | | |
| 39 | 183-4 | 54.43 | 54.27 | 3.84 | 3.77 | 16.91 | 17.07 | 13.36 | 13.07 | 11.14 | 11.41 | | | | |
| 40 | 49-61 | 58.41 | 57.43 | 3.61 | 3.56 | | | 10.75 | 10.11 | | | | | | |
| 41 | 153-6 | 55.44 | 55.62 | 4.19 | 4.21 | 16.36 | 17.46 | 12.93 | 12.32 | 11.08 | 10.15 | | | F | 4.89/5.28 |
| 42 | 40-2 | 61.87 | 61.02 | 4.15 | 4.50 | 18.26 | 18.54 | 10.82 | 10.61 | | | | | | |
| 43 | 168-171 | 58.86 | 58.99 | 3.86 | 3.98 | 15.10 | 14.97 | 11.93 | 11.17 | 10.22 | 10.75 | | | | |
| 44 | oil | 57.16 | 55.85 | 4.45 | 4.48 | 24.10 | 23.50 | 14.28 | 13.65 | | | | | | |
| 45 | 189-192 | 54.78 | 54.94 | 5.41 | 5.43 | 28.54 | 28.16 | 11.36 | 11.44 | | | | | | |
| 46 | oil | 61.72 | 59.35 | 6.04 | 6.22 | 20.24 | 19.30 | 12.00 | 10.98 | | | | | | |
| 47 | oil | 62.64 | 61.13 | 6.36 | 6.60 | 19.46 | 19.53 | 11.53 | 10.66 | | | | | | |
| 48 | oil | 63.49 | 61.07 | 6.66 | 6.75 | 18.74 | 19.00 | 11.11 | 9.90 | | | | | | |
| 49 | 134-7 | 58.46 | 58.31 | 4.91 | 4.82 | 23.01 | 23.01 | 13.63 | 13.33 | | | | | | |
| 50 | 48-52 | 66.34 | 65.17 | 5.31 | 5.68 | 17.80 | 17.13 | 10.55 | 9.21 | | | | | | |
| 51 | 62-5 | 70.91 | 69.82 | 5.01 | 5.28 | 11.02 | 11.01 | 13.06 | 12.19 | | | | | | |
| 52 | oil | 49.13 | 48.06 | 3.87 | 4.11 | 36.26 | 10.74 | 11.36 | | | | | | | |
| 53 | 121-3 | 61.80 | 61.40 | 6.71 | 6.78 | | | 16.96 | 17.04 | 14.53 | 14.37 | | | | |
| 54 | 224(dec) | 45.60 | 45.58 | 4.27 | 4.33 | | | 9.96 | 10.00 | | | | | | |
| 55 | 130(dec) | 52.43 | 51.46 | 4.65 | 4.50 | 17.20 | 16.54 | 10.19 | 9.98 | 15.52 | 17.93 | | | | |
| 56 | 149-51 | 62.96 | 59.14 | 6.16 | 5.70 | | | 12.24 | 11.07 | 18.64 | 23.30 | | | | |
| 57 | 127-8 | 64.41 | 64.28 | 6.08 | 5.90 | | | 18.78 | 18.65 | 10.73 | 10.97 | | | | |
| 58 | 78-80 | 82.49 | 80.65 | 5.48 | 5.36 | | | 12.02 | 12.18 | | | | | | |

Some of the aralkyl and diarylalkylnitriles which are used as intermediates in the preparation of the compounds of this invention are commercially available materials. In Table III below some of the representative aralkyl and diarylalkylnitriles which are prepared via the methods of this invention are given along with their melting points or boiling points and elemental analyses.

TABLE II

X—⟨phenyl⟩—CHCN
         |
         R$^1$

| X | R$^1$ | Empirical Formula | b.p./mm(m.p.) | C T | C F | H T | H F | Cl T | Cl F | N T | N F | O T | O F |
|---|---|---|---|---|---|---|---|---|---|---|---|---|---|
| 2,4-Cl$_2$ | C$_4$H$_9{}^n$ | C$_{12}$H$_{13}$Cl$_2$N | 105-7/0.1 | 59.52 | 59.53 | 5.41 | 5.60 | 29.28 | 28.84 | 5.78 | 5.80 | | |
| H | C$_4$H$_9{}^n$ | C$_{12}$H$_{15}$N | 75/.03 | 83.19 | 83.43 | 8.73 | 8.90 | — | — | 8.08 | 8.30 | | |
| 2,6-Cl$_2$ | C$_4$H$_9{}^n$ | C$_{12}$H$_{13}$Cl$_2$N | 164-184/.03 | 59.52 | 59.88 | 5.41 | 5.73 | 29.28 | 29.35 | 5.78 | 5.65 | | |
| 2,4-Cl$_2$ | C$_6$H$_4$ | C$_{14}$H$_9$Cl$_2$N | 147-165/.03 | 64.15 | 64.04 | 3.46 | 3.53 | 27.05 | 26.86 | 5.34 | 4.85 | | |
| 2,4-Cl$_2$ | CO$_2$C$_2$H$_5$ | C$_{11}$H$_9$Cl$_2$NO$_2$ | 107-115/.05 | 51.19 | 51.68 | 3.51 | 3.72 | 27.47 | 27.21 | 5.43 | 5.41 | 12.40 | 12.44 |
| 2,4-Cl$_2$ | COCH$_3$ | C$_{10}$H$_7$Cl$_2$NO | (130-131°) | 52.66 | 52.73 | 3.09 | 3.00 | 31.09 | 30.96 | 6.14 | 6.14 | 7.01 | 7.30 |
| 4-Cl | 4-ClC$_6$H$_4$ | C$_{14}$H$_9$Cl$_2$N | (80-83°) | 64.15 | 63.65 | 3.46 | 3.41 | 27.05 | 27.26 | 5.34 | 5.03 | | |
| 2,4-CH$_3$ | C$_4$H$_9{}^n$ | C$_{14}$H$_{19}$N | 100-4/.05 | 83.53 | 83.20 | 9.51 | 9.80 | | | 6.96 | 7.22 | | |
| 2-CH$_3$ | C$_4$H$_9{}^n$ | C$_{13}$H$_{17}$N | 69-78/.05 | 83.37 | 83.42 | 9.15 | 9.08 | | | 7.48 | 7.70 | | |

The arylcyanoalkyl and diarylcyanoalkylimidazoles of this invention are highly reactive broad spectrum fungicidal agents. These compounds are particularly effective against phytopathogenic fungi such as grey mold (*Botrytis cinerea*) on broad bean plants (*Vicia faba*), bean powdery mildew (*Erysiphe polygoni*) on broad bean plants (var. Dwarf Hort.) tomato late blight (*Phytophthora infestans*) on tomato seedlings, rice blast (*Piricularia oryzae*) on rice plants, grape downy mildew (*Plasmopora viticola*) on grape seedlings, barley net blotch (*Helminthosporium teres*) on barley plants, wheat leaf rust (*Puccinia recondita*) on wheat plants and wheat stem rust (*Puccinia graminis* f. sp. *tritici*) on wheat plants.

The following test procedures are used to evaluate compounds, acid addition salts and metal salt complexes of this invention. In the evaluation of these fungicidal agents against *Botrytis cinerea* the following procedure is followed. Broad beans are trimmed to a height of approximately 4-5 inches 24 hours prior to chemical application, the plants are sprayed to run off with the chemical agent and allowed to dry. The plants are inoculated with *Botyrtis cinerea* and incubated in a humid environment at 75°–85° F. for 66 hours. The plant lesions are evaluated 66 to 68 hours after inoculation.

The effect of these fungicidal agents against *Erysiphe polygoni* is evaluated via the following procedure. In this test, bean plants (var. Dwarf Hort.) are thinned to two plants per pot 24 hours prior to chemical application. *Erysiphe polygoni* is cultured on bean leaves for 20–21 days under existing greenhouse conditions. Spores are harvested by adding deionized water containing 0.05 ml. of Tween 80 per 500 ml. water to a quart jar containing excised mildew infected bean leaves. The spores are loosened from the leaf surface by shaking the jar. The resulting suspension is filtered through cheesecloth to remove plant debris and adjusted to $2\text{–}2.5 \times 10^4$ spores per ml. Bean plants are inoculated by spraying the leaves and stems with inoculum until a film of inoculum is observed on the plants. Inoculated plants are maintained under existing greenhouse conditions. Treatment comparisons are made 8–10 days after inoculation. Typical bean powdery mildew symptons are circular white mycelial mats (fructifications) on the leaf surface.

In evaluating these fungicidal agents against *Phytophthora infestans* the following procedure is utilized. Tomato seedlings are sprayed to run-off with suspensions of agents under evaluation in the given dosage series. The sprayed plants are allowed to dry and are then inoculated with a suspension of *Phytophthora infestans* fungal spores. The plants are maintained at 60° to 62° F. temperature and 100% relative humidity for about 40 hours to incubate. The plants are then stored under greenhouse conditions for 5 or 6 days at which time treatment comparisons are made.

The test for evaluating these fungicidal agents against *Piricularia oryzae* is given below. Rice plants are trimmed to a height of approximately 5 inches 24 hours prior to chemical application. The plants are sprayed to run-off with the chemical agent, allowed to dry, and then inoculated with *Piricularia oryzae* and maintained in a humid environment (75°–85° F.) for 24 hours. The plants are then maintained in a greenhouse environment for 7–8 days after inoculation at which time disease readings are made.

The effect of these fungicidal agents against *Plasmopora viticola* is evaluated via the following procedure. Grape seedlings are sprayed to run-off with suspensions of agents under evaluation in the given dosage series. The sprayed plants are allowed to dry and then inoculated with a suspension of the *Plasmopora viticola* fungal spores. The inoculated plants are incubated in a humid environment at 65°–70° F. for 48 hours then stored in light for 4 days and replaced into a humid environment (65°–70° F.) for 24 hours. The plants are then evaluated for fungal growth.

In evaluating these fungicidal agents against *Helminthosporium teres* the following procedure is followed. Barley plants are trimmed to a height of approximately 2.5 inches 24 hours prior to chemical application. The plants are sprayed to run-off with the chemical agent and allowed to dry. The plants are then inoculated with *Helminthosporium teres* and incubated in a humid environment at 75° to 80° F. for 24 hours. The plants are then transferred to a greenhouse (70°–75° F.) for 6 to 7 days prior to determining disease control levels.

Another test used to evaluate the broad spectrum of activity possessed by these fungicidal agents is their control of *Puccinia recondita*. In this test the wheat plants are trimmed to approximately 2.5 inches prior to chemical application to afford uniform height and ease of inoculation. The plants are sprayed to run-off as before and dried before inoculation. The inoculated plants are placed in humid a environment at 70°–75° F. for 24 hours then placed in the greenhouse at 70°–75° F. for 6 to 8 days. The occurrence of rust colored pustules on the surface of the leaves is evaluated. In the test for *Puccinia graminis* f. sp. *tritici*, seven-day-old wheat plants (var. Monon) are trimmed to approximately 2.5 inches, 24 hours prior to chemical application. The plants are sprayed to run-off and dried before inoculation. The wheat plants are then inoculated by applying a stem rust spore suspension containing a minimum of $2.5 \times 10^5$ spores per ml until run-off. After inoculation the plants are placed into a humid environment at approximately 68° F., and the temperature is not allowed to exceed 85° F. After two weeks, treatment comparisons are made. The wheat stem rust is characterized by brick red spores in irregularly shaped sori on the leaves and stems of the wheat seedlings.

The results of the above tests in evaluating the arylcyanoalkyl and diarylcyanoalkylimidazoles, and their acid addition salts and metal salt complexes are shown in Table III. In compiling this table, the following codes are used:

BOT = Grey mold of broad beans (*Botrytis cinerea*)
BPM = Bean powdery mildew (*Erysiphe polygoni*)
TLB = Tomato late blight (*Phytophthora infestans*)
RB = Rice blast (*Piricularia oryzae*)
GDM = Grape downy mildew (*Plasmopora viticola*)
BH = Barley Net Blotch (*Helminthosporium teres*)
WLR = Wheat leaf rust (*Puccinia recondita*)
WSR = Wheat stem rust (*Puccinia graminis* f.sp. *tritici*)

The following disease rating scale is used for evaluating these fungicidal agents:

A = 97–100% disease control
B = 90–96% disease control
C = 70–89% disease control
D = 50–69% disease control
E = >50% disease control Table III

| Ex. No. | BH | BOT | BPM | GDM | RB | TLB | WLR | WSR |
|---|---|---|---|---|---|---|---|---|
| 1 | A | C | A | E | E | E | A | B |
| 2 | E | E | A | B | B | E | A | |
| 3 | A | B | A | B | A | E | A | |
| 4 | A | E | A | B | | B | A | |
| 5 | A | D | A | B | E | B | A | |
| 6 | E | C | A | E | | E | | A |
| 7 | E | E | A | E | | E | | A |
| 8 | E | C | E | E | | E | | E |
| 9 | A | B | A | E | | E | | A |
| 10 | E | C | A | E | | E | | A |
| 11 | | E | A | B | E | E | E | |
| 12 | A | E | A | E | E | C | A | |
| 13 | | A | A | E | | E | | E |
| 14 | A | B | A | B | B | E | A | |
| 15 | A | B | A | B | A | B | C | |
| 16 | A | E | A | B | | E | E | |
| 17 | A | E | A | B | B | E | A | |
| 18 | E | C | E | E | E | E | | E |
| 19 | E | C | A | E | | E | | C |
| 20 | E | B | A | E | | E | | C |
| 21 | E | E | E | C | B | A | | B |
| 22 | A | C | A | E | | E | | E |
| 23 | E | E | A | E | | E | | E |
| 24 | A | A | A | B | E | E | A | |
| 25 | A | E | E | E | B | E | E | |
| 26 | A | A | A | E | B | B | E | |

Table III-continued

DISEASE LEVEL (300 PPM)

| Ex. No. | BH | BOT | BPM | GDM | RB | TLB | WLR | WSR |
|---|---|---|---|---|---|---|---|---|
| 27 | A | E | A | B | B | E | E | |
| 28 | E | E | A | B | B | E | C | |
| 29 | A | C | A | B | A | E | E | |
| 30 | E | E | E | E | B | E | E | |
| 31 | C | A | A | E | B | E | B | |
| 32 | E | A | E | E | | B | | B |
| 33 | A | A | A | E | | B | | B |
| 34 | A | E | A | C | A | E | | A |
| 35 | B | B | A | E | | E | | E |
| 36 | C | E | A | E | B | E | | E |
| 37 | A | E | A | E | E | E | E | |
| 38 | A | E | E | B | B | A | E | |
| 39 | E | C | A | A | B | B | A | |
| 40 | B | B | A | A | | E | | C |
| 41 | A | A | A | B | B | B | A | |
| 42 | E | A | A | C | | B | | B |
| 43 | E | B | A | C | | E | | E |
| 44 | E | E | A | B | | B | E | |
| 45 | E | E | E | E | A | E | | E |
| 46 | E | E | E | B | B | E | C | |
| 47 | E | E | E | B | B | E | E | |
| 48 | E | E | E | B | B | E | E | |
| 49 | E E | A | A | E | E | | E | |
| 50 | C | E | A | C | | C | | C |
| 51 | C | B | A | C | | E | | A |
| 52 | E | E | E | E | A | E | | E |
| 53 | E | E | E | E | E | E | | E |
| 54 | A | B | A | A | A | E | A | |
| 55 | A | A | A | B | A | B | B | |
| 56 | A | B | A | A | A | E | B | |
| 57 | E | E | E | E | E | E | E | |

The arylcyanoalkyl and diarylcyanoalkylimidazoles are not only broad spectrum fungicides but possess protectant and eradicant activity as well. The eradicant fungicidal properties of the compounds of this invention are particularly unique in that they kill phytophathogenic fungi in infected plant tissues and therefore can be utilized after fungal infection has already occurred. The compounds of this invention also possess excellent fungicidal control of wheat stem rust (*Puccinia graminis*) and barley net blotch (*Helminthosporium teres*) and exhibit excellent eradicant activity on barley net blotch (*Helminthosporium teres*) and wheat yellow spot (*Helminthosporium tritici-vulgaris*).

The aryl and diarylcyanoalkylimidazoles and their metal salt complexes are useful as agricultural fungicides and as such can be applied to various loci such as the seed, the soil, or the foliage. For such purposes these compounds and their metal salt complexes can be used in the technical or pure form as prepared, as solutions or as formulations. The compounds or metal salt complexes are usually taken up in a carrier or are formulated so as to render them suitable for subsequent dissemination as fungicides. For example, they can be formulated as wettable powders, emulsifiable concentrates, dusts, granular formulations, aerosols, or flowable emulsion concentrates. In such formulations, the compounds or complexes are extended with a liquid or solid carrier and, when desired, suitable surfactants are incorporated.

It is usually desirable, particularly in the case of foliar spray formulations, to include adjuvants, such as wetting agents, spreading agents, dispersing agents, stickers, adhesives and the like in accordance with agricultural practices. Such adjuvants commonly used in the art can be found in the John W. McCutcheon, Inc., publication "Detergents and Emulsifiers, Annual."

In general, the compounds and complexes of this invention can be dissolved in certain solvents such as acetone, methanol, ethanol, dimethylformamide, pyridine or dimethyl sulfoxide and such solutions extended with water. The concentration of the solution can vary from 1% to 90% with a preferred range being 5 to 50%.

For the preparation of emulsifier concentrates, the compound can be dissolved in suitable organic solvents, or a mixture of solvents, together with an emulsifying agent which permits dispersion of the fungicide in water. The concentration of the active ingredient in emulsifiable concentrates is usually 10% to 90% and in flowable emulsion concentrates, this can be as high as 75%.

Wettable powders suitable for spraying, can be prepared by admixing the compound with a finely divided solid, such as clays, inorganic silicates and carbonates, and silicas and incorporating wetting agents, sticking agents, and/or dispersing agents in such mixtures. The concentration of active ingredients in such formulations is usually in the range of 20% to 98%, preferably 40% to 75%. A typical wettable powder is made by blending 50 parts of the zinc chloride complex of 1-[2-cyano-2,2-diphenylethyl]imidazole with 45 parts of a synthetic precipitated hydrated silicon dioxide sold under the trademark name of Hi-Sil®, and 5 parts of sodium lignosulfonate (Marasperse® N-22). In another preparation of kaolin type (Barden) clay is used in place of the Hi-Sil in the above wettable powder, and in another such preparation 25% of the Hi-Sil is replaced with a synthetic sodium silico aluminate sold under the trademark Zeolex® 7.

Dusts are prepared by mixing the aryl or diarylcyanoalkyl imidazole or its metal salt complex with finely divided inert solids which can be organic or inorganic in nature. Materials useful for this purpose include botanical flours, silicas, silicates, carbonates and clays. One convenient method of preparing a dust is to dilute a wettable powder with a finely divided carrier. Dust concentrates containing 20% to 80% of the active ingredient are commonly made and are subsequently diluted in 1% to 10% use concentration.

The aryl or diarylcyanoalkylimidazole or their metal salt complexes can be applied as fungicidal sprays by methods commonly employed, such as conventional high-gallonage hydraulic sprays, low-gallonage sprays, air-blast spray, aerial sprays and dusts. The dilution and rate of application will depend upon the type of equipment employed, the method of application and diseases to be controlled, but the preferred effective amount is usually about 0.1 lb. to 25 lbs. per acre of the active ingredient.

As a seed protectant, the amount of toxicant coated on the seed is usually at a dosage rate of about 0.1 to 20 ounces per hundred pounds of seed. As a soil fungicide the chemical can be incorporated in the soil or applied to the surface usually at a rate of 0.1 to 50 lbs. per acre. As a foliar fungicide, the toxicant is usually applied to growing plants at a rate of 0.25 to 10 lbs. per acre.

Fungicides which can be combined with the fungicides of this invention includes:

(a) Dithiocarbamates and derivatives such as:

ferric dimethyldithiocarbamate (ferbam),
zinc dimethyldithiocarbamate (ziram),
manganese ethylenebisdithiocarbamate (maneb)
and its coordination product with zinc ion (mancozeb), zinc ethylenebisdithiocarbamate (zineb), zinc propylenebisdithiocarbamate (propineb), sodium methyldithiocarbamate (metham), tetramethylthiuram disulfide (thiram), and 3,5-dimethyl-1,3,5-2H-tetrahydrothiadiazine-2-thione (dazomet);

(b) Nitrophenol derivatives such as:

dinitro-(1-methylheptyl)phenyl crotonate (dinocap),
2-sec-butyl-4,6-dinitrophenyl 3,3-dimethyl acrylate (binapacryl), and
2-sec-butyl-4,6-dinitrophenyl isopropyl carbonate;

(c) heterocyclic structures such as:

N-trichloromethylthiotetrahydro-phthalimide (captan),
N-trichloromethylthiophthalimide (folpet),
2-heptadecyl-2-imidazoline acetate (glyodin),
2-octylisothiazolone-3,
2,4-dichloro-6-(o-choloranilino)-s-triazine,
diethyl phthalimidophosphorothioate,
4-butyl-1,2,4-triazole,
5-amino-1-[bis(dimethylamino)phosphinyl]-3-phenyl-1,2,4-triazole
5-ethoxy-3-trichloromethyl-1,2,4-thiadiazole,
2,3-dicyano-1,4-dithiaanthraquinone (dithianon),
2-thio-1,3-dithio-[4,5-b]quinoxaline (thioquinox),
methyl 1-(butylcarbamoyl)-2-benzimidazole carbamate (benomyl),
2-(4-thiazolyl)benzimidazole (thiabendazole)
4-(2-chlorophenylhydrazono)-3-methyl-5-isoxazolones,
pyridine-2-thiol-1-oxide,
8-hydroxyquinoline sulfate,
2,3-dihydro-5-carboxanilido-6-methyl-1,4-oxathiin-4,4-dioxide,
2,3-dihydro-5-carboxanilido-6-methyl-1,4-oxathiin,
α(phenyl)-α(2,4-dichlorophenyl)-5-pyrimidinyl-methanol (triarimol),
cis-N-[(1,1,2,2-tetrachloroethyl)thio]-4-cyclohexene-1,2-dicarboximide,
3-[2-(3,5-dimethyl-2-oxycyclohexyl)-2-hydroxyethyl]-glutarimide (cycloheximide),
dehydroacetic acid,
N-(1,1,2,2-tetrachloroethylthio)-3a,4,7,7a-tetrahydrophthalimide (captafol),
6-butyl-2-ethylamino-4-hydroxy-6-methylpyrimidine (ethirimol),
acetate of 4-cyclododecyl-2,6-dimethylmorpholine (dodemorph), and
6-methyl-2-oxo-1,3-dithiolo[4,5-b]-quinoxaline (quinomethionate).

(d) miscellaneous halogenated fungicides such as:

tetrachloro-p-benzoquinone (chloranil),
2,3-dichloro-1,4-naphthoquinone (dichlone),
1,4-dichloro-2,5-dimethoxybenzene (chloroneb),
3,5,6-trichloro-o-anisic acid (tricamba),
2,4,5,6-tetrachloroisophthalonitrile (TCPN),
2,6-dichloro-4-nitroaniline (dicloran),
2-chloro-1-nitropropane,
polychloronitrobenzenes such as:
pentachloronitrobenzene (PCNB) and
tetrafluorodichloroacetone;

(e) fungicidal antibiotics such as:

griseofulvin,
kasugamycin and
streptomycin;

(f) copper-based fungicides such as:

cuprous oxide,
basic cupric chloride,
basic copper carbonate,
copper naphthenate, and
Bordeaux mixture; and (g) miscellaneous fungicides such as:

diphenyl,
dodecylguanidine acetate (dodine),
phenylmercuric acetate,
N-ethylmercuri-1,2,3,6-tetrahydro-3,6-endomethano-3,4,5,6,7,7-hexachlorophthalimide,
phenylmercuric monoethanol ammonium lactate,
p-dimethylaminobenzenediazo sodium sulfonate,
methyl isothiocyanate,
1-thiocyano-2,4-dinitrobenzene,
1-phenylthiosemicarbazide,
nickel-containing compounds
calcium cyanamide,
lime sulfur,
sulfur, and
1,2-bis(3-methoxycarbonyl-2-thioureido)benzene (thiophanate-methyl).

The metal salt complexes of this invention can be advantageously employed in various ways. Since these compounds and metal salt complexes possess inherent systemicity and broad spectrum fungicidal activity, they can be employed in the storage of cereal grain. These compounds and complexes can also be employed as fungicides in turf and fruit orchard applications. Other applications of the compounds and metal salt complexes of this invention will suggest themselves to those skilled in the art of agriculture and horticulture.

We claim:

1. A metal salt complex of the formula:

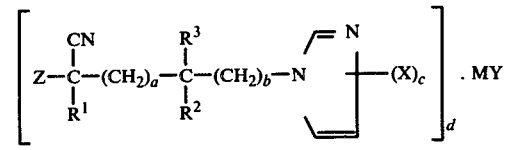

wherein z is phenyl optionally substituted with up to three substituents selected from the group consisting of fluoro, chloro, bromo, iodo, nitro, cyano, methoxy, ethoxy, methyl, ethyl, propyl, butyl, trihalomethyl, phenyl and benzoyl; $R^1$ is hydrogen, ($C_1$-$C_{20}$) alkyl, ($C_3$-$C_8$) cycloalkyl, ($C_5$-$C_8$) cycloalkenyl, ($C_3$-$C_6$) alkenyl, ($C_3$-$C_6$) alkynyl, phenyl, benzyl or phenethyl or phenyl, benzyl or phenethyl substituted with up to three substituents independently selected from the group consisting of fluoro, chloro, bromo, iodo, nitro, cyano, methoxy, ethoxy, methyl, ethyl and trihalomethyl; $R^2$ and $R^3$ are independently hydrogen, ($C_1$-$C_{20}$) alkyl, phenyl, benzyl or phenethyl or phenyl, benzyl or phenethyl substituted with up to three substituents independently selected from the group consisting of fluoro, chloro, bromo, iodo, nitro, cyano, methoxy, ethoxy, methyl, ethyl and trihalomethyl or when taken together form ($C_4$-$C_8$) cycloalkyl; $R^1$ and Z when taken together form the group

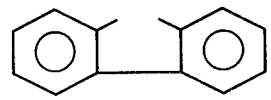

a is 0 to 5; b is 0 to 5; X is halogen; c is zero to 2; M is a metal cation selected from Mg, Ca, Ba, Sn, Pb, Cu, Zn, Cd, Cr, Mn, Fe, Co and Ni; Y is an anion counterion selected from the group consisting of chloride, bromide, iodide, sulfate, bisulfate, phosphate, nitrate, perchlorate, carbonate, bicarbonate, hydrosulfide, hydroxide, acetate, oxalate, malate, citrate, tartarate, or alkylene dithiocarbamate and d is 1 to 4.

2. A metal salt complex according to claim 1 wherein Z is phenyl or phenyl substituted with up to two substituents selected from the group consisting of fluoro, nitro, methoxy and methyl.

3. A metal salt complex according to claim 2 wherein $R^1$ is hydrogen, $(C_1-C_{10})$ alkyl; $(C_3-C_8)$ cycloalkyl, $(C_5-C_8)$ cycloalkenyl, $(C_3-C_6)$ alkenyl, $(C_3-C_6)$ alkynyl, phenyl, benzyl or phenethyl or phenyl, benzyl or phenethyl substituted with up to two substituents selected from the group consisting of chloro, nitro, methoxy and methyl.

4. A metal salt complex according to claim 3 wherein $R^2$ and $R^3$ are independently hydrogen, $(C_1-C_{10})$ alkyl, phenyl, benzyl or phenethyl or phenyl, benzyl or phenethyl substituted with up to two substituents selected from the group consisting of chloro, nitro, methoxy or methyl or when taken together form $(C_4-C_8)$ cycloalkyl.

5. A metal salt complex according to claim 3 wherein $R^2$ and $R^3$ are independently hydrogen, $(C_1-C_{10})$ alkyl or phenyl.

6. A metal salt complex according to claim 4 wherein X is chloro and c is 2.

7. A metal salt complex according to claim 4 wherein c is zero.

8. A metal salt complex according to claim 5 wherein a is 0 to 5 and b and c are zero.

9. A metal salt complex according to claim 5 wherein a, b and c are zero.

10. A metal salt complex according to claim 1 wherein $R^1$ is n-butyl, a, b and c are zero and $R^2$ and $R^3$ are hydrogen.

11. A method for controlling phytopathogenic fungi which comprises applying an effective amount of a metal salt complex according to claim 1 to a plant, to plant seeds or to the plant habitat.

12. A method according to claim 11 wherein the metal salt complex is applied to the plant or the plant habitat at the rate of 0.1 to 50 lbs. per acre.

13. A method according to claim 12 wherein the compound is applied to the plant seeds at a rate of 0.1 to 20 ounces per hundred pounds of seed.

14. A fungicidal composition for controlling phytopathogenic fungi which comprises an agronomically acceptable carrier and, as the active ingredient, an effective amount of a metal salt complex of claim 1.

* * * * *